(12) United States Patent
Huh

(10) Patent No.: US 10,441,019 B2
(45) Date of Patent: Oct. 15, 2019

(54) FUNCTIONAL/MULTI-PURPOSE HEAD CUSHION FOR HEADBAND

(71) Applicant: OTOS WING. CO., LTD., Seoul (KR)

(72) Inventor: Sung-Won Huh, Seoul (KR)

(73) Assignee: OTOS WING. CO., LTD., Seoul (KR)

(*) Notice: Subject to any disclaimer, the term of this patent is extended or adjusted under 35 U.S.C. 154(b) by 93 days.

(21) Appl. No.: 15/309,665

(22) PCT Filed: Mar. 13, 2015

(86) PCT No.: PCT/KR2015/002479
§ 371 (c)(1),
(2) Date: Nov. 8, 2016

(87) PCT Pub. No.: WO2015/174627
PCT Pub. Date: Nov. 19, 2015

(65) Prior Publication Data
US 2017/0150771 A1    Jun. 1, 2017

(30) Foreign Application Priority Data
May 15, 2014    (KR) .................. 10-2014-0058353

(51) Int. Cl.
*A42B 3/32*    (2006.01)
*A42B 3/12*    (2006.01)
(Continued)

(52) U.S. Cl.
CPC .............. *A42B 3/324* (2013.01); *A42B 3/085* (2013.01); *A42B 3/12* (2013.01); *A42B 3/14* (2013.01); *A61F 9/06* (2013.01)

(58) Field of Classification Search
CPC ........... A42B 3/085; A42B 3/12; A42B 3/145; A42B 3/324; A42B 3/14; A42B 3/142;
(Continued)

(56) References Cited

U.S. PATENT DOCUMENTS 3,018,483 A * 1/1962 Monroeville .......... A42B 3/145
                                                              2/417
4,986,282 A    1/1991 Stackhouse et al.
(Continued)

FOREIGN PATENT DOCUMENTS

JP    2001-336020 A    12/2001
JP    2009-203569 A     9/2009

OTHER PUBLICATIONS

International Search Report (in English and Korean) for PCT/KR2015/002479, ISA/KR, Daejeon, dated Jun. 25, 2015.
(Continued)

*Primary Examiner* — Alissa J Tompkins
*Assistant Examiner* — Brieanna Szafran
(74) *Attorney, Agent, or Firm* — Harness, Dickey & Pierce, P.L.C.

(57) ABSTRACT

The present invention relates to a functional/multi-purpose head cushion for a headband; the headband is formed from a head cushion comprising: a main body which is depressively formed from up, down, left and right towards the central part; a fixing clip which is provided on the upper part of the main body and is inserted into the band main body or the support band; and banding members for integrally connecting both end portions of the fixing clip and the upper edge portions of the main body, wherein the head cushion is formed from a resilient material so as to have easy shape transformation and resilience and is insert-provided inside the headband and thereby assist in supporting a wearer's head.

15 Claims, 12 Drawing Sheets

(51) Int. Cl.
*A61K 9/06* (2006.01)
*A42B 3/08* (2006.01)
*A42B 3/14* (2006.01)
*A61F 9/06* (2006.01)

(58) Field of Classification Search
CPC ........... A42B 3/147; A42B 3/127; A42B 3/00; A42B 3/04; A61F 9/06; A45D 8/20
USPC ............ 2/414, 416–421, 174; 132/276
See application file for complete search history.

(56) References Cited

U.S. PATENT DOCUMENTS

| | | | | |
|---|---|---|---|---|
| 5,042,093 | A | * | 8/1991 | Legendre ............... A42B 3/145 2/419 |
| 5,774,900 | A | * | 7/1998 | Wu ........................ A42B 3/06 2/171.3 |
| 2005/0138719 | A1 | * | 6/2005 | Huh ........................ A42B 3/14 2/416 |
| 2010/0050324 | A1 | * | 3/2010 | Musal .................... A42B 3/085 2/417 |
| 2010/0229286 | A1 | | 9/2010 | Ahlgren et al. |
| 2010/0281603 | A1 | * | 11/2010 | Ho ........................... A42B 3/04 2/411 |
| 2011/0083240 | A1 | * | 4/2011 | Crye ..................... A42B 3/085 2/2.5 |
| 2013/0239303 | A1 | * | 9/2013 | Cotterman ............... A42B 3/08 2/417 |

OTHER PUBLICATIONS

Written Opinion of the ISA (Korean) for PCT/KR2015/002479, ISA/KR, Daejeon, dated Jun. 25, 2015.

\* cited by examiner

FUNCTIONAL/MULTI-PURPOSE HEAD CUSHION FOR HEADBAND

CROSS REFERENCE TO RELATED APPLICATIONS

This application is a 371 U.S. National Stage of International Application No. PCT/KR2015/002479, filed Mar. 13, 2015, which claims the benefit of and priority to Korean Patent Application No. 10-2014-0058353, filed May 15, 2014. The entire disclosures of the above applications are incorporated herein by reference.

TECHNICAL FIELD

The present invention relates to a head cushion, and more particularly, a functional/multi-purpose head cushion for a headband, installed at a headband inside a welding mask (a welding face shield), a safety face shield, a hard hat, a helmet, or a medical helmet and configured to assist wearing of the headband to improve wearability when the headband is worn on the head of a wearer.

BACKGROUND ART

Generally, industrial safety equipment such as a welding mask (a welding face shield), a safety face shield, a hard hat, a helmet or the like are products used in various industrial fields, and a medical head guard, a safety hat, a medical helmet or the like are medical supplies for preventing an accident which may occur while a worker or a wearer is working.

A welding mask among the industrial safety equipment described above is used for preventing various accidents such as sparking of a parent metal toward the face of a worker caused by a strong flash and instantaneous high heat and resistance which occur during a welding operation.

When a worker wears a welding mask on his or her head as described above, the vision and face of the worker may be protected from an accident such as sparking of a parent metal for welding toward the face of the worker while the worker is working.

Meanwhile, the welding mask described above includes a welding face shield for protecting the face of a worker and a headband for being worn on the head of a worker.

That is, the welding mask includes a welding face shield with a transparent window for protecting the vision and face of a worker from an accident while being worn and a headband provided inside the welding face shield worn on the head of the worker for fixing the welding face shield thereto.

As shown in FIGS. 1 to 3, the headband described above includes a first band portion 110 which surrounds a perimeter of the head of a wearer and is formed to be in close contact with the forehead, and a second band portion 130 and a third band portion 150 for surrounding the front region and occipital region of the head.

Here, a headband 100 includes a length adjusting lever 170 configured to touch the occipital region of the wearer, and the length adjusting lever 170 is connected to an end portion of the first band portion 110 using a length adjusting band (not shown).

Here, as a general technology in the art, the length adjusting lever 170 is connected while both end portions of the length adjusting band connected to the end portion of the first band portion 110 are inserted in left and right sides and an elongated hole with sawteeth is formed at the length adjusting band to be coupled with the length adjusting lever.

Meanwhile, the length adjusting lever 170 includes a cushion member adhered to an inner surface thereof to come into close contact with the occipital region of a worker.

Since the cushion member is provided at the inner surface of the length adjusting lever as described above, the cushion member surrounds the occipital region of a worker while the worker wears the headband, thereby providing convenience of wearing a welding mask including the headband and simultaneously providing comfortability.

Since the headband described above is configured to directly touch a particular portion of the head of the wearer, wearability is decreased. Since the second band portion and the third band portion pressurize and press the particular portion of the head, an unpleasant feeling, headache, and the like occur when the headband is worn for a long time.

To solve such problems described above, a worker inserts a certain sized piece of paper, fabric or the like as a slip sheet above the head where the second band portion and the third band portion of the headband installed at a welding mask and the like are positioned as a temporary expedient to prevent the second band portion and the third band portion from pressurizing or pressing a particular portion of the head. However, the piece of paper, fabric or the like inserted as the slip sheet is not fixed to the inside of the headband and is separated or comes out therefrom and it is necessary to repetitively prepare pieces of paper or fabric formed as a slip sheet.

Due to this, inconvenience such as working after newly inserting and installing paper or fabric inserted as a slip sheet in the headband while working and the like interrupts continuous working, thereby reducing working efficiency and effectiveness.

Also, it is inconvenient to repetitively remove and reinstall paper or fabric inserted as a slip sheet in a headband when industrial safety equipment such as a welding mask and the like is detached or attached to take a break or to restart working and the paper or fabric inserted as a slip sheet may be easily lost due to carelessness of a worker.

Also, since sweat generated at the head of a worker while working is absorbed by paper or fabric inserted in and installed at a headband as a slip sheet, the paper or fabric is contaminated such as occurrence of an odor and the like not to be reused. Due to this, it is necessary to insert and install a new piece of paper or fabric as a slip sheet and it is difficult to repetitive reuse the paper or fabric.

DISCLOSURE OF INVENTION

Technical Problem

The present invention provides a functional/multi-purpose head cushion for a headband, installed at a band body or a supporting band of the headband to assist supporting the head of a wearer to be easily detachable and replaceable from industrial safety equipment such as a welding mask (a welding face shield), a safety face shield, a hard hat, a helmet and the like and medical supplies such as a medical head guard, a safety hat, a medical helmet and the like, formed of a flexible elastic material, extending a supported range of the head and simultaneously reducing a contact area therebetween by including openings to minimize a pressure on the head such as a vulnerable place and the like, easily performing ventilation and airing at the headband to minimize perspiration while the wearer works for a long time, having improved flexibility due to incised portions to be easily modified in shape and restored and sequentially/gradually worn on the head of the wearer, easily improving wearability and distributing a load to easily support the entire head while worn, preventing and buffering pressure, easily coming into close contact with the head and simultaneously strongly maintaining a close contact state regardless of a shape and size of the head, applied while being variously modified depending on situations by using an auxiliary pad formed of paper or fabric mounted on the head cushion, and applicable to a general headband.

Technical Solution

One aspect of the present invention provides a functional/multi-purpose head cushion for a headband including a band body configured to be worn on a head of a wearer, a supporting band connected to the band body and supported by the top of the head of the wearer, an adjustable band connected to a rear end of the band body and configured to be adjusted in length, and a length adjusting lever configured to adjust a length of the adjustable band. The head cushion includes a main body formed to be concave from top, bottom, left, and right toward the center thereof, a fixing clip provided at an upper portion of the main body and inserted into the band body or the supporting band, and a bent member connecting both end portions of the fixing clip with an upper portion of an edge of the main body to be integrated therewith. Here, the head cushion includes an elastic material to be easily modified and restored in shape, inserted, and installed in the headband to complementarily support the head of the wearer.

Here, at least one opening may be formed to pass through the main body.

Also, at least one incised portion may be formed at the main body.

Here, at least one bent portion may be formed at the main body to be bent in a semicircular shape.

Also, a bent section bent by a certain angle may be formed at an edge end portion of the main body.

Meanwhile, a soft portion including a soft material may be formed at a bottom surface of the main body.

Here, an auxiliary pad mounted at a lower portion of the main body and including a paper or fabric material may be provided.

Also, the fixing clip may be formed in a staple shape with an insertion hole at one side thereof to enable the band body or the supporting band to be inserted and installed therein.

Meanwhile, the fixing clip may be formed in a U shape with an insertion hole at a top thereof to enable the band body or the supporting band to be inserted and installed therein.

Also, at least one separation-preventing section may be formed to protrude from the insertion hole.

Here, the separation-preventing section may be formed in a wedge shape including an incline formed at one side to enable the band body or the supporting band to be inserted therein and a preventing surface formed at the other side to prevent the band body or the supporting band inserted therein from being separated therefrom.

Also, at least one bent hole in a slot shape may be formed to pass through the bent member.

Advantageous Effects

According to embodiments of the present invention, a head cushion may be applied to a general headband in industrial safety equipment such as a welding mask (a welding face shield), a safety face shield, a hard hat, a helmet and the like and medical supplies such as a medical head guard, a safety hat, a medical helmet and the like to obtain an economic effect, may improve wearability by assisting supporting the head of a wearer, may minimize a pressure on the head and simultaneously improve a buffering effect by extending a supported range of the head and reducing a contact area therebetween, may minimize perspiration while working by easily performing ventilation and airing at the headband, may easily support the entire head by distributing a load due to improved flexibility, may prevent and simultaneously buffer pressure, may be easily modified in shape and restored to sequentially/gradually come into contact with the head, may easily come into close contact with the head and simultaneously strongly maintain a close contact state regardless of a shape and size of the head of the wearer, may employ an auxiliary pad formed of paper or fabric depending on situations, may be easily installed and released to be easily detachable from the headband and simultaneously easily replaceable, may be installed at a position needed by the wearer and simultaneously changed in position by a simple operation, and may be easily installed and maintained in a fixed state to increase working efficiency and effectiveness.

BEST MODE FOR INVENTION

Hereinafter, exemplary embodiments of the present invention will be described in detail with reference to the attached drawings. Also, the embodiments are not intended to limit the scope of the present invention but are merely provided as examples, and may be variously changed without departing from the technical concept of the present invention.

Figure 1:
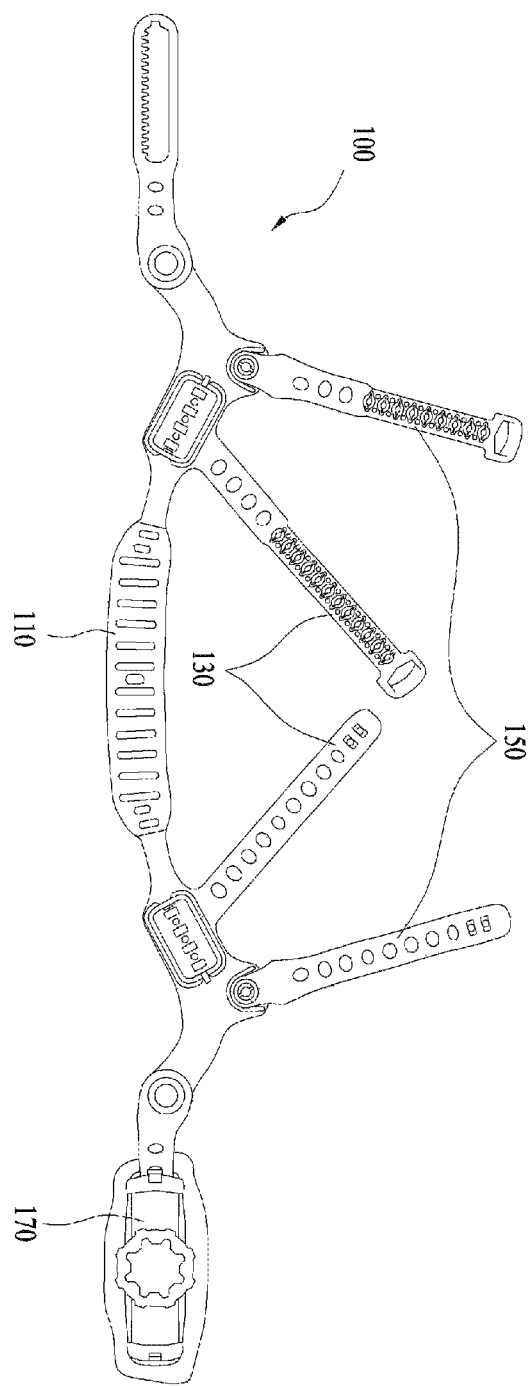
FIG. 1 is a planar figure schematically illustrating a headband according to a conventional technology.
Figure 2:
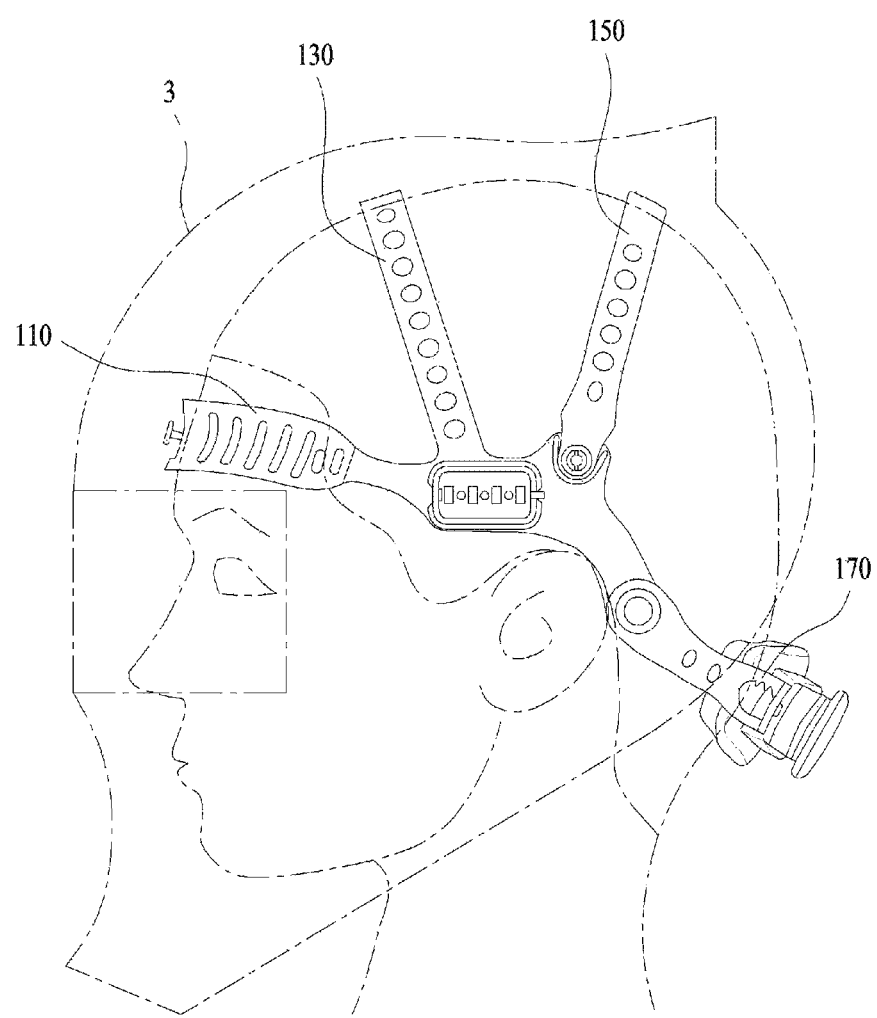
FIG. 2 is a perspective view schematically illustrating a state in which the headband according to the conventional technology is worn.
Figure 3:
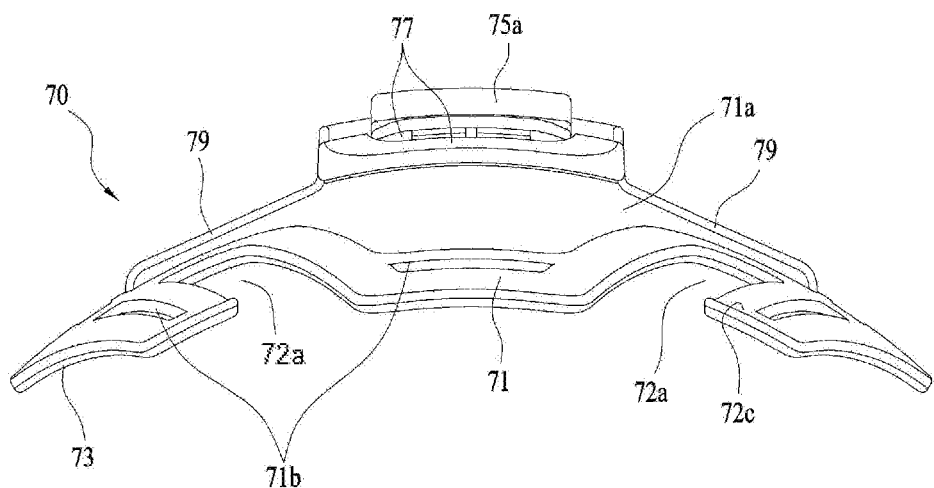
FIG. 3 is a front view schematically illustrating a functional/multi-purpose head cushion for a headband according to the present invention.
Figure 4:
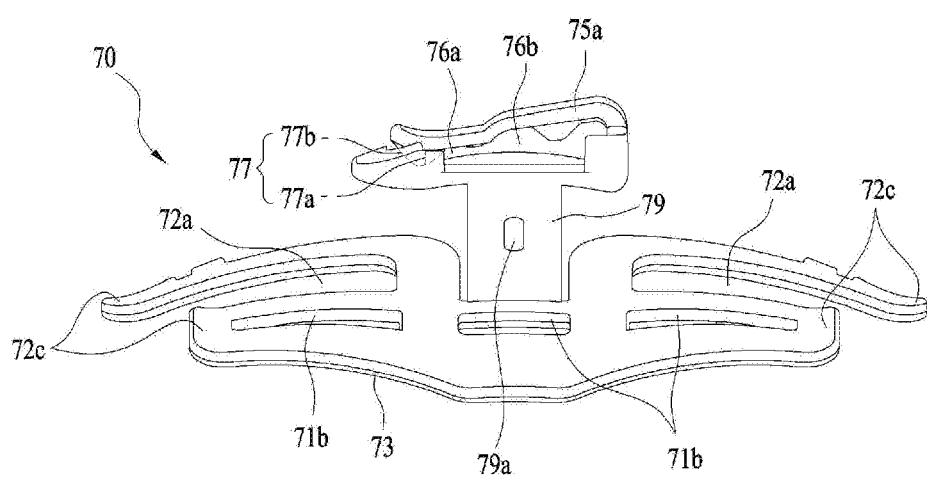
FIG. 4 is a side view schematically illustrating the functional/multi-purpose head cushion for a headband according to the present invention.
Figure 5:
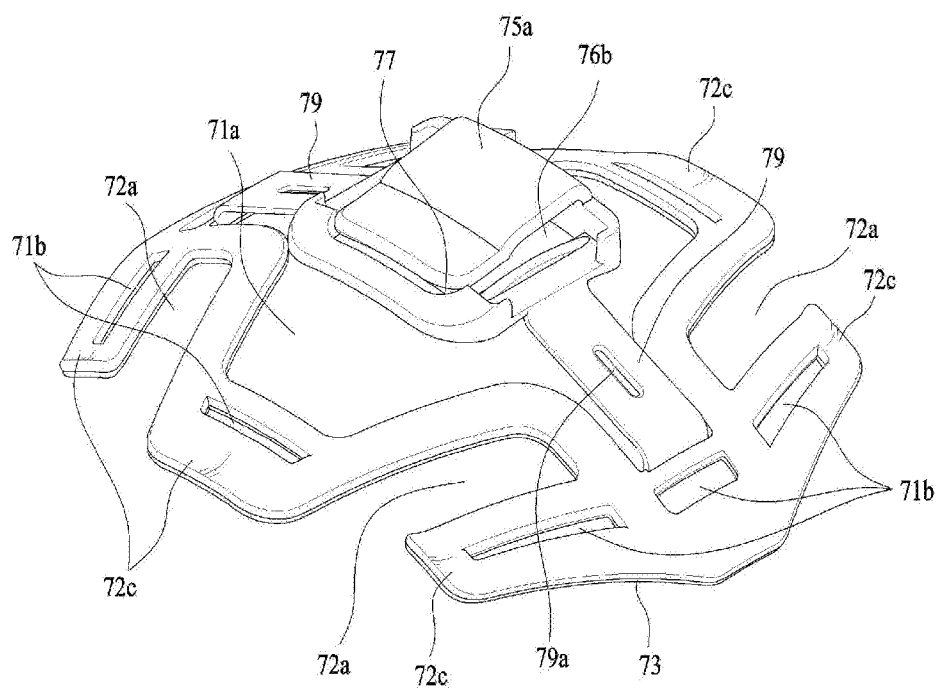
FIG. 5 is a perspective view schematically illustrating the functional/multi-purpose head cushion for a headband according to the present invention.
Figure 6:
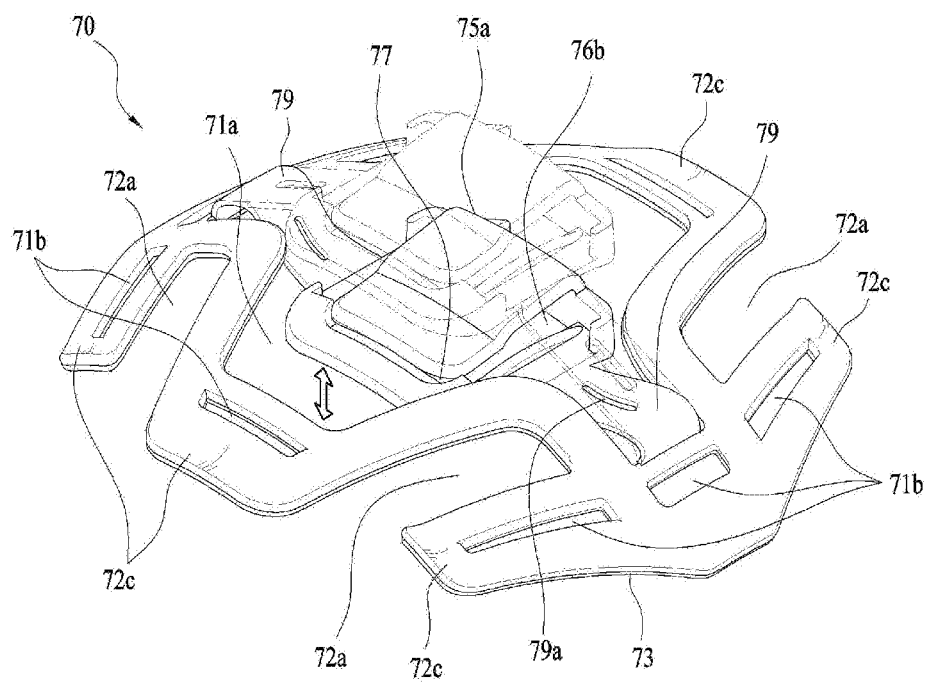
FIG. 6 is a perspective view schematically illustrating a modified shape of the functional/multi-purpose head cushion for a headband according to the present invention.
Figure 7:
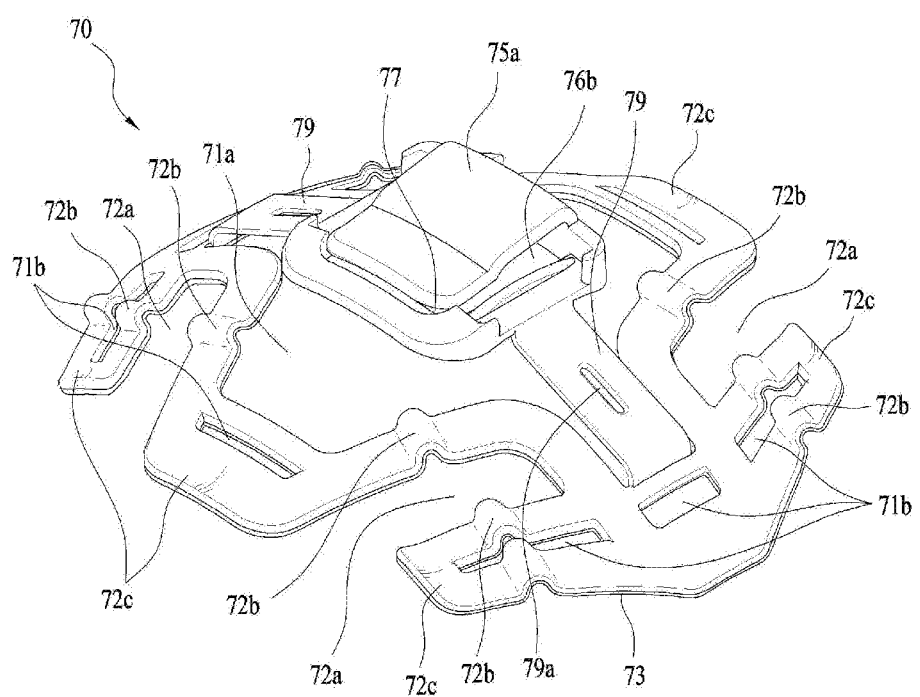
FIG. 7 is a perspective view schematically illustrating one embodiment of the functional/multi-purpose head cushion for a headband according to the present invention.
Figure 8:
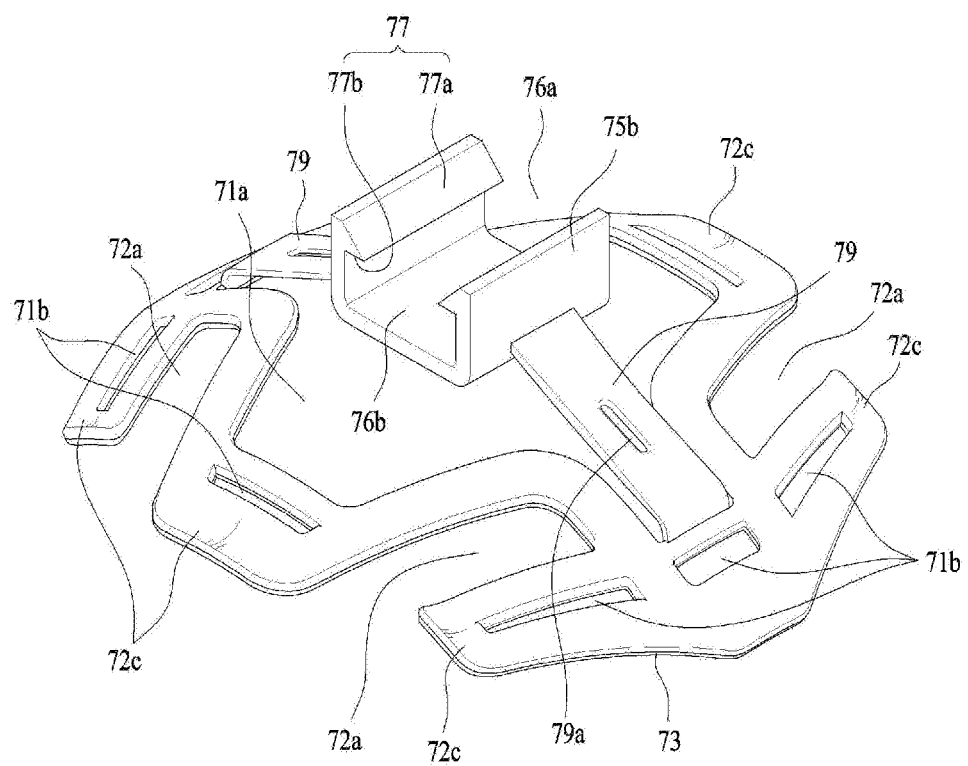
FIG. 8 is a perspective view schematically illustrating another embodiment of the functional/multi-purpose head cushion for a headband according to the present invention.
Figure 9:
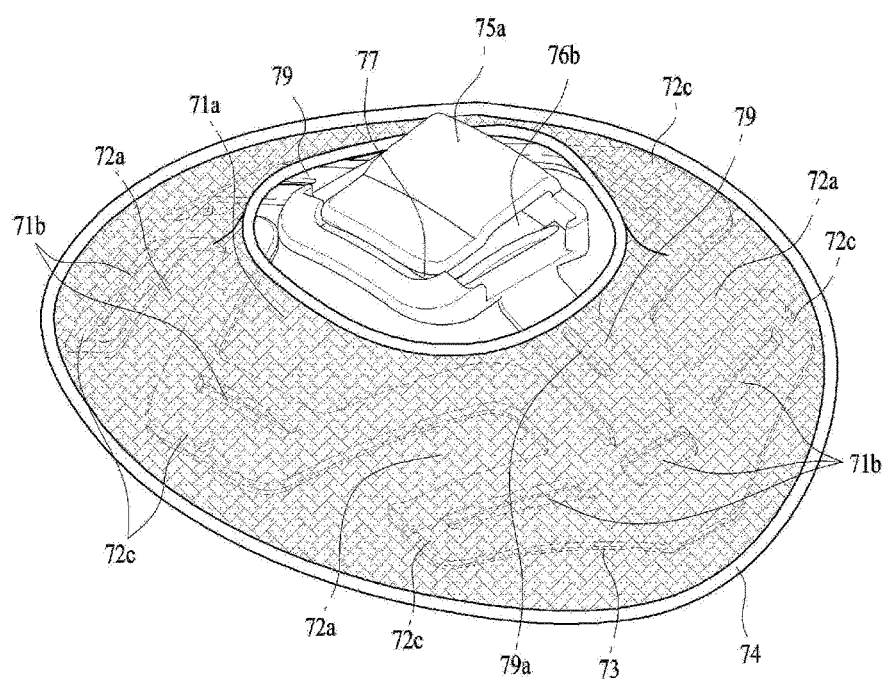
FIG. 9 is a perspective view schematically illustrating still another embodiment of the functional/multi-purpose head cushion for a headband according to the present invention.
Figure 10:
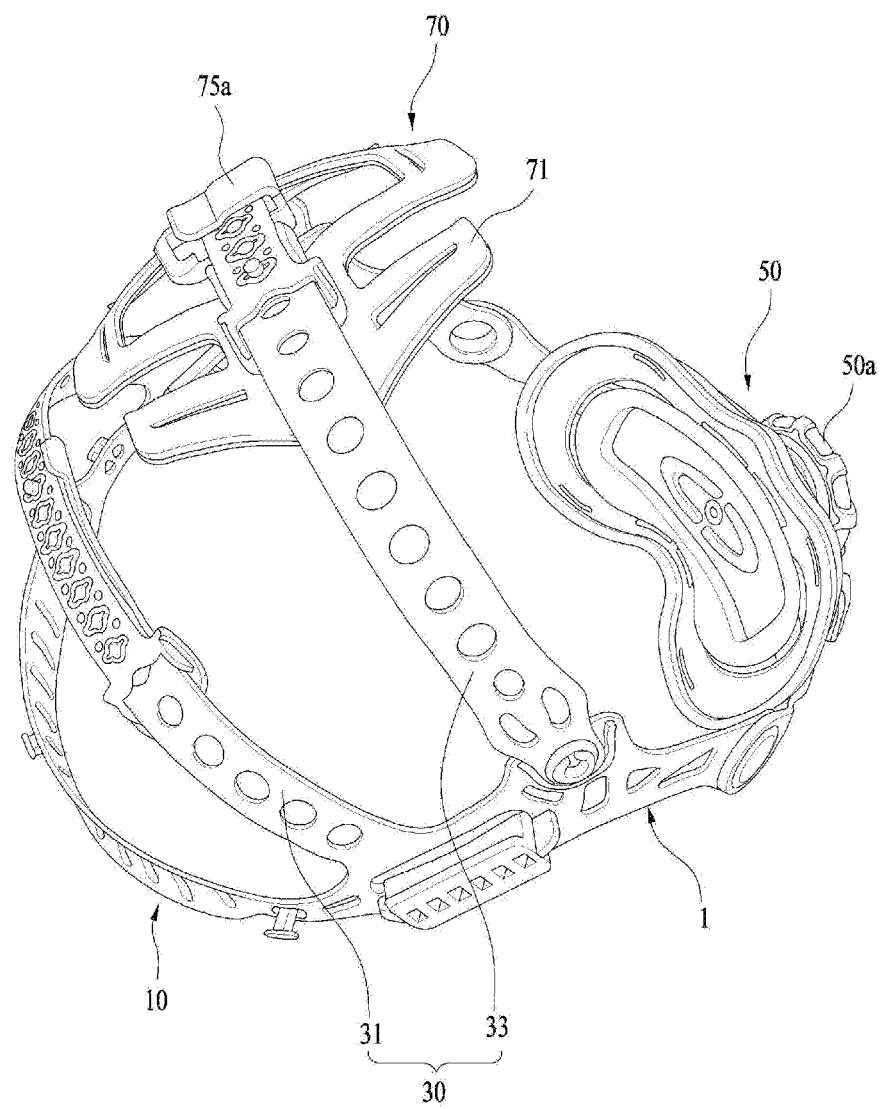
FIGS. 10 and 11 are perspective views schematically illustrating states in which the functional/multi-purpose head cushion for a headband according to the present invention is mounted on a headband.
Figure 11:
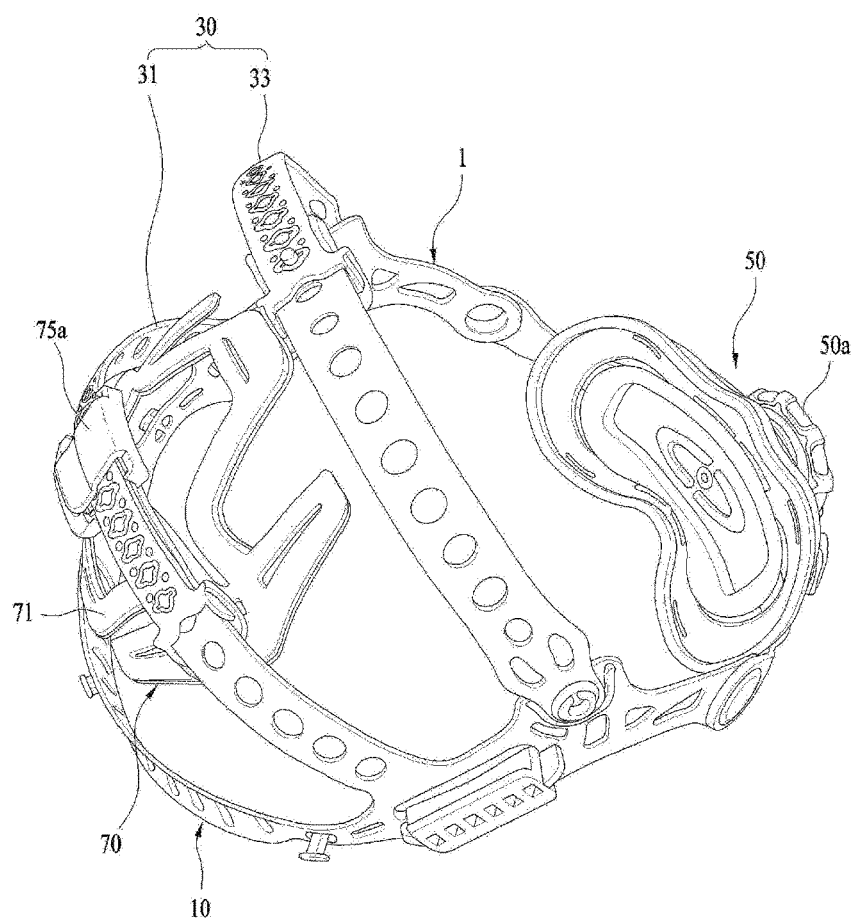
Figure 12:
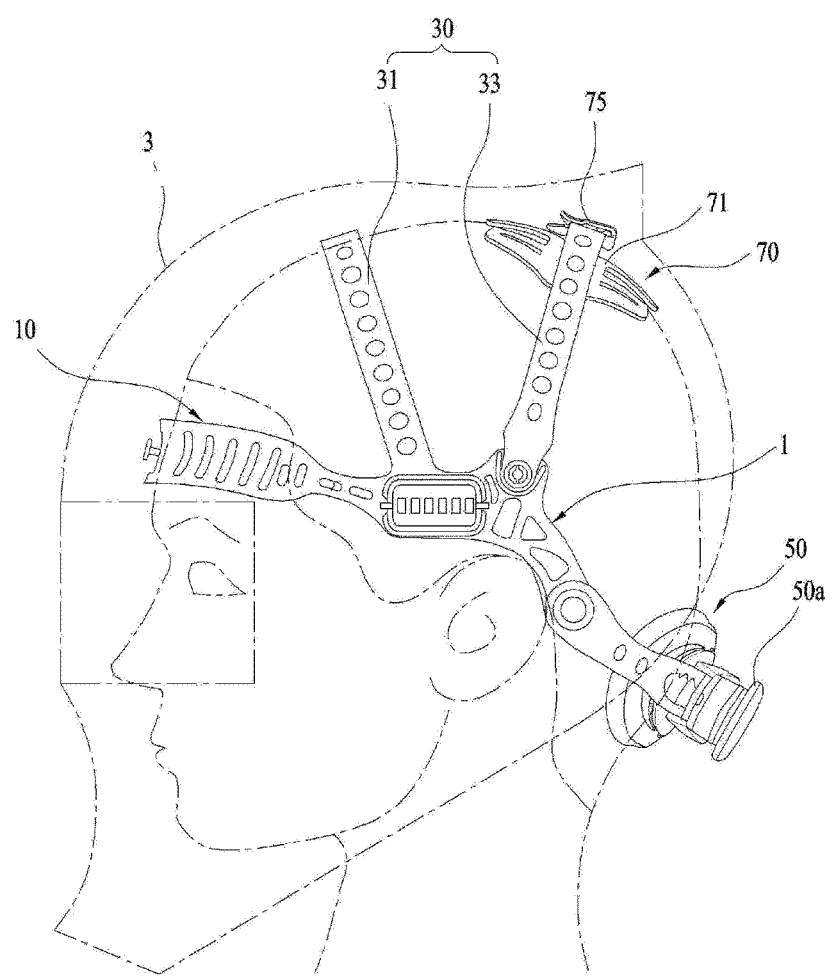
FIGS. 12 and 13 are side views schematically illustrating states in which a headband on which the functional/multi-purpose head cushion for a headband according to the present invention is mounted is worn.
Figure 13:
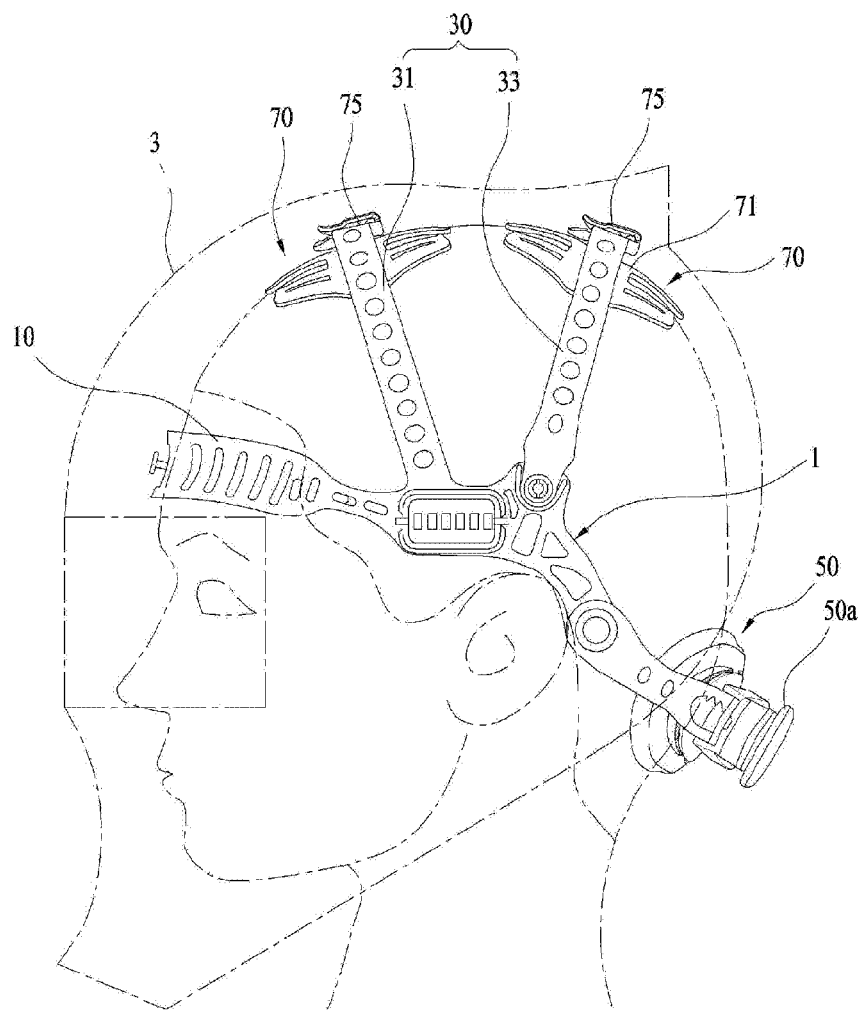

FIG. 3 is a front view schematically illustrating a functional/multi-purpose head cushion for a headband according to the present invention, FIG. 4 is a side view schematically illustrating the functional/multi-purpose head cushion for a headband according to the present invention, FIG. 5 is a perspective view schematically illustrating the functional/multi-purpose head cushion for a headband according to the present invention, FIG. 6 is a perspective view schematically illustrating a modified shape of the functional/multi-purpose head cushion for a headband according to the present invention, FIG. 7 is a perspective view schematically illustrating one embodiment of the functional/multi-purpose head cushion for a headband according to the present invention, FIG. 8 is a perspective view schematically illustrating another embodiment of the functional/multi-purpose head cushion for a headband according to the present invention, FIG. 9 is a perspective view schematically illustrating still another embodiment of the functional/multi-purpose head cushion for a headband according to the present invention, FIGS. 10 and 11 are perspective views schematically illustrating states in which the functional/multi-purpose head cushion for a headband according to the present invention is mounted on a headband, and FIGS. 12 and 13 are side views schematically illustrating states in which a headband on which the functional/multi-purpose head cushion for a headband according to the present invention is mounted is worn.

As shown in the drawings, a functional/multi-purpose head cushion 70 for a headband according to the present invention is applied to a headband 1 in industrial safety equipment, such as a welding mask 3 (a welding face shield), a safety face shield, a hard hat, a helmet and the like, and medical supplies, such as a medical head guard, a safety hat, a medical helmet and the like.

That is, the head cushion 70 is installed in the headband 1 applied to industrial safety equipment, such as the welding mask 3, a safety face shield, a hard hat, a helmet and the like, and medical supplies, such as a medical head guard, a safety hat, a medical helmet and the like, for preventing an accident while working.

Here, the headband 1 includes a band body 10 for being worn on the head of a wearer, an adjustable band 20 connected to both end portions of the band body 10 and adjusted in length according to a size and a perimeter of the head of the wearer, a supporting band 30 extending over the band body 10 and positioned at a top of the head of the wearer to support the band body 10, and a length adjusting lever 50 inserted into and coupled to both end portions of the adjustable band 20 and configured to adjust a length of the adjustable band 20.

Here, the adjustable band 20 includes an elongated hole (not shown) in a slot shape with sawteeth at each of the both end portions thereof. The both end portions of the adjustable band 20 are inserted into and coupled to left and right sides of the length adjusting lever 50, and the length of the adjustable band 20 is adjusted by forwardly rotating or a backwardly rotating a lever 50a of the length adjusting lever 50.

Here, since components and operations of the length adjusting lever 50 provided at the headband 1 are included in a general technology in the art, a detailed description thereof will be omitted.

Meanwhile, a coupling hole (not shown) for coupling to the welding mask 3 is formed at the adjustable band 20 positioned at both sides of the forehead of the wearer, and the welding mask 3 is rotatably coupled to the coupling hole of the adjustable band 20 using a hinge (not shown).

Also, the supporting band 30 includes a first supporting band 31 provided in front of the adjustable band 20 and positioned at an upper portion of a frontal region of the wearer and a second supporting band 33 provided behind the first supporting band 33 and positioned at the top of the wearer.

Due to the structure described above, when the headband 1 is worn, the adjustable band 20 is worn on the head of the wearer, the first supporting band 31 of the supporting band 30, which extends from the adjustable band 20, is positioned at the top of the frontal region of the wearer to support the head, the second supporting band 33 is positioned at the top of the wearer to support the head, and the length of the adjustable band 20 is adjusted by the length adjusting lever 50 to be adequate for a perimeter and size of the head of the wearer.

Here, the head cushion 70 provides a comfortable fit while the headband 1 is worn by enlarging a supported area of the head of the wearer, distributing a weight and load concentrated on the head of the wearer, and improving ventilation and airing is provided at the band body 10 or the supporting band 30 of the headband 1.

For this, the head cushion 70 is formed of an elastic material to be easily modified and restored in shape when pressurized and released, and includes a main body 71, fixing clips 75a and 75b, and a bent member 79 connecting the fixing clips 75a and 75b to the main body 71.

The main body 71 is an elastic plate-shaped body formed to be concave from top, bottom, left, and right sides toward the center thereof.

Here, one or more openings 71a and 71b are formed to pass through the main body 71. That is, a plurality of such openings 71a and 71b are formed to pass through the main body 71 of the head cushion 70 touching the head of the wearer when the head cushion 70 applied to the headband 1 is worn.

Since the openings 71a and 71b are formed to pass through the main body 71 as described above, a supporting range of the main body 71 of the head cushion 70 and the head is enlarged and a contact area between the main body 71 and the head is reduced so that wearability and comfortability may be increased, and pressure and pain at a central portion of the head touching the main body 71 of the head cushion 70 may be prevented while simultaneously distributing a weight and load of the welding mask 3 and the like to release pressure on the wearer.

Also, the head cushion 70 may easily come into close contact with the head of the wearer regardless of a shape of the head while simultaneously strongly maintaining a close contact state by the openings 71a and 71b.

Here, the openings 71a have a large size and are formed to pass through a central portion of the main body 71 touching the top of the wearer's head, and the openings 71b have a slot shape with a smaller size than the opening 71a formed at the central portion and are formed to pass through a peripheral portion of the main body 71.

Since the openings 71a are formed at the central portion of the main body 71 as described above, contact between a portion of the center of the head vulnerable to pain and the head cushion 70 may be prevented when the head cushion 70 is worn for a long time.

In one embodiment of the present invention, the size of the openings 71a formed to pass through the central portion of the main body 71 is formed to be greater than the size of the openings 71b formed to pass through the peripheral portion. However, the size of the openings 71a formed to pass through the central portion of the main body 71 may be formed to be smaller than the size of the openings 71b formed to pass through the peripheral portion, or the size of the openings 71a formed to pass through the central portion of the main body 71 may be formed to be identical to the size of the openings 71b formed to pass through the peripheral portion Also, in one embodiment of the present invention, the openings 71a with the large size are formed to pass through the central portion of the main body 71 and the openings 71b with the smaller size than that of the openings 71a at the central portion are formed to pass through the peripheral portion. However, the sizes, shapes, and positions of the openings 71a and 71b formed to pass through the main body 71 may be variously changeable and are not limited thereto.

Meanwhile, at least one incised portion 72a is formed at the main body 71. That is, a plurality of such incised portions 72a are formed at the main body 71 of the head cushion 70 touching the head of the wearer when the head cushion 70 applied to the headband 1 is worn.

Since the incised portions 72a are formed at the main body 71 as described above, the head cushion 70 may flexibly come into contact with the head of the wearer while being worn and the weight and load of the welding mask 3 and the like may be easily distributed to release pressure on the wearer.

Also, since flexibility is added to the main body 71 and elastic efficiency is increased by the incised portions 72a, the head cushion 70 is flexibly bent upward, downward, leftward, and rightward while being worn to come into close contact with the head of the wearer head regardless of the size and shape of the head and is flexibly bent according to the weight and load of the welding mask 3 after being worn, thereby easily performing an operation and improving working efficiency and effectiveness.

In one embodiment of the present invention, four incised portions 72a are formed at positions and with sizes and shapes symmetrical to each other based on a side of the main body 71. However, the positions, sizes, shapes, and numbers of the incised portions of the incised portions 72a may be changed.

Meanwhile, in one embodiment of the present invention, the openings 71a and 71b and the incised portions 72a are formed at the main body 71. However, according to usage, only the openings 71a and 71b or only the incised portions 72a may be formed to pass through the main body 71.

Here, ventilation and airing at the head of the wearer are easily performed by the formed openings 71a and 71b formed to pass through the main body 71 of the functional/multi-purpose head cushion 70 for a headband according to the present invention while the headband 1 is worn, and due to this perspiration while working may be minimized.

Meanwhile, in one embodiment of the present invention, there is provided a structure in which the main body 71 of the head cushion 70 is flexibly bent upward, downward, leftward, and rightward while being simultaneously flexibly bent according to a weight and load by increasing elastic efficiency using the openings 71a and 71b or the incised portions 72a formed at the main body 71 of the head cushion 70. However, as shown in FIG. 7, at least one bent portion 72b is formed to be bent at the main body 71 of the head cushion 70 to further improve flexibility of the main body 71.

That is, the bent portions 72b are frames (not shown) of the main body 71 of the head cushion 70, are formed to be an approximately frame-shaped body due to the openings 71a and 71b and the incised portions 72a, and are formed to be bent in a semicircular shape.

As described above, since the openings 71a and 71b, the incised portions 72a, and the bent portions 72a are formed at the main body 71 of the head cushion 70, a weight and load may be more easily distributed while simultaneously improving the elastic efficiency of the main body 71 so that the main body 71 may be bent upward, downward, leftward, rightward, and in various directions to provide wearability and comfortability and maintain a state of being in comfortably close contact with the head after being worn regardless of a movement such as operation.

In one embodiment of the present invention, the bent portions 72b formed at the frame of the main body 71 are formed to be bent in a semicircular shape. However, as long as elastic efficiency and flexibility are easily increased, the bent portions 72b may be formed at the main body 71 in a wedge shape or various other shapes.

Also, in one embodiment of the present invention, one bent portion 72b is formed to be bent in a semicircular shape in a longitudinal direction of the frame of the main body 71. However, a plurality of such bent portions 72b may be formed to be bent in a longitudinal direction of each of the frames.

Also, in one embodiment of the present invention, the bent portion 72b is formed at the frame of the body 71 to be bent in a semicircular shape with a blocked upper portion and an open lower portion. However, the bent portion 72b may be formed in a semicircular shape with an open upper portion and a blocked lower portion. The bent portions 72b may be formed so that the bent portions 72b in a semicircular shape with the blocked upper portion and the open lower portion and the bent portions 72b in a semicircular shape with the open upper portion and the blocked lower portion are alternately formed, but the present invention is not limited thereto.

Meanwhile, a bent section 72c bent by a certain angle is formed at an edge end of the main body 71. That is, the bent section 72c is formed by bending the edge end of the main body 71 of the head cushion 70 directly touching the head of the wearer by the certain angle.

Since the bent section 72c is formed by bending the edge end of the main body 71 touching the head of the wearer first by the certain angle as described above, the head cushion 70 may be stably worn and mounted on the head while being worn while simultaneously preventing an accident such as a scratch and the like at the head caused by the edge end.

Here, the bent section 72c formed to be bent at the edge end of the main body 71 may be bent by various angles and in various shapes, and more particularly, the bent section 72c coming into direct contact with and directly touching the head of the wearer may be bent in a round shape.

Meanwhile, a soft portion 73 formed of a soft material is formed at a bottom surface of the main body 71. That is, the soft portion 73 formed of a soft material is formed at the bottom surface of the head cushion 70 coming into contact with and touching the head of the wearer when the head cushion 70 according to the present invention is installed in the headband 1 and worn.

Here, the soft portion 73 may be formed at the bottom surface of the main body 71 through double injection molding but is not limited thereto.

Since the soft portion 73 formed of a soft material is formed at the bottom surface of the main body 71 as described above, the head of the wearer touches the soft portion while the head cushion 70 is worn, thereby minimizing a pressure on the head of the wearer caused by the weight and load and simultaneously preventing the head cushion 70 from falling from the head.

Here, a protrusions (not shown) in an embossed shape may be formed to protrude from the soft portion 73 or grooves (not shown) in a semicircular shape may be formed. The protrusions or grooves formed at the soft portion 73 as described prevent the head cushion 70 from falling off or being separated and simultaneously perform acupressure, ventilation and airing functions.

In the embodiment, the protrusions in the embossed shape or the grooves in the semicircular shape are formed at the soft portion 73. However, the shape of the protrusions or grooves is not limited thereto and may be variously changed and the number of the protrusions or grooves formed at the soft portion 73 may also be variously changed.

Meanwhile, in one embodiment of the present invention, the soft portion 73 formed of a soft material is formed at the bottom surface of the main body 71 to minimize the pressure on the head of the wearer while the head cushion 70 is worn. However, as shown in FIG. 9, according to need and requirement of the wearer, an auxiliary pad 74 formed of paper or fabric may be provided at a bottom of the main body 71.

That is, the auxiliary pad 74 formed of paper or fabric mounted at the bottom of the main body 71 and configured to include a space (not shown) in which the main body 71 is inserted and positioned and which is formed therein and an inlet (not shown) having elasticity formed at a top thereof.

Since the auxiliary pad 74 is installed at the bottom of the main body 71 of the head cushion 70 and used according to the need or requirement of the wearer as described above, the pressure on the head of the wearer such as the weight, load and the like may be prevented.

Also, since formed to be separable from the head cushion 70, the auxiliary pad 74 may be repetitively reused through washing and the like. Also, the auxiliary pad 74 is formed of paper or fabric in one embodiment of the present invention but is not limited thereto.

Meanwhile, a bent member (not shown) in a stepped shape may be formed to extend from the edge end of the main body 71. That is, the bent member formed to be bent several times in a stepped shape may extend from the edge end of the main body 71 in a vertical direction.

Since the bent member in the stepped shape is formed to extend from the edge end of the main body 71 as described above, when the head cushion 70 is worn, the bent member formed in the stepped shape at the end portion of the head cushion 70 first coming into contact with the head of the wearer is folded and comes into close contact and the like with the head of the wearer to be sequentially/gradually worn thereon, thereby distributing and simultaneously buffering the weight and load.

In the embodiment, the bent member in the stepped shape formed to be bent several times is formed at the edge end of the main body 71 of the head cushion 70. As long as a portion first coming into contact with the head of the wearer is folded and comes into close contact with the head of the wearer to be easily and gradually worn thereon while the head cushion 70 is worn, the bent member may be formed at the edge end of the main body 71 of the head cushion 70 in a zigzag shape, a pantograph shape, or a wave shape and the shape of the bent member is not limited thereto.

Here, at least one incised portion (not shown) may be formed in a vertical direction at the bent member in the stepped shape formed to extend downward from the edge end of the main body 71 of the head cushion 70 in such a way that the portion in contact with the head of the wearer may be separately folded and come into close contact therewith.

Since a plurality of such incised portions are formed at the bent member formed to be bent in the stepped shape at the edge end of the main body 71 of the head cushion 70 and the bent member branches into a plurality of pieces, a portion among the bent member branching into the plurality of pieces first coming into contact with the head of the wearer is separately and gradually folded and comes in close contact therewith, thereby improving wearability and simultaneously distributing the weight and load.

Here, the number and shape of incised portions formed at the bent member formed to be bent in the stepped shape at the edge end of the main body 71 of the head cushion 70 may be variously changed and a length and width of the incised portion may be variously changed.

In one embodiment of the present invention, the main body 71 is formed in a concave shape from a top, bottom, left, and right sides toward the center thereof. However, the main body 71 may be formed to be bent in such a way that a side cross section thereof may be formed in an approximate staple shape to come into close contact with the head of the wearer regardless of the shape and size thereof.

The fixing clip 75a is provided at a top of the main body 71 and the band body 10 or the supporting band 30 is inserted and installed therein. For this, the fixing clip 75a includes an insertion hole 76a formed at a top for enabling the band body 10 or the supporting band 30 to be inserted therein and an installation space 76b in which the band body 10 or the supporting band 30 inserted through the insertion hole 76a is installed, which is formed in an approximately ⊏-shape alternately arranged at both top and bottom of a center thereof.

Here, the installation space 76b formed at the fixing clip 75a may be formed in a size for preventing the band body 10 or the supporting band 30 inserted to be installed from being separated and released but is not limited thereto.

Here, at least one separation-preventing section 77 is formed to protrude from the insertion hole 76a of the fixing clip 75a. That is, at least one separation-preventing section 77 is formed to protrude from the end portion of the insertion hole 76a to prevent the band body 10 or the supporting band 30 from being separated and released when the band body 10 or the supporting band 30 is inserted to be installed through the insertion hole 76a of the fixing clip 75a.

Also, the separation-preventing section 77 is formed to protrude from each of both sides of an end portion of the insertion hole 76a of the fixing clip 75a alternately arranged at top and bottom.

Here, the separation-preventing section 77 is formed to in a wedge shape to allow the band body 10 or the supporting band 30 to be easily inserted and to prevent the inserted band body 10 or supporting band 30 from being separated and released. That is, at least one separation-preventing section 77 including an incline 77a formed at one side and a preventing surface 77b formed at the other side is formed to protrude from the end portion of the insertion hole 76a to prevent the band body 10 or the supporting band 30 from being separated and released when the band body 10 or the supporting band 30 is inserted to be installed.

In one embodiment of the present invention, the separation-preventing section 77 is formed in the wedge shape. However, as long as the band body 10 or the supporting band 30 is easily inserted to be installed in the installation space 76*b* through the insertion hole 76*a* and is prevented from being separated and released, the shape of the separation-preventing section 77 may be variously changed.

Here, in one embodiment of the present invention, the number of separation-preventing sections 77 formed to protrude from a top and bottom of the insertion hole 76*a* may be variously changed.

As described above, it becomes easier to maintain a state in which the band body 10 or the supporting band 30 inserted into the installation space 76*b* through the insertion hole 76*a* is inserted to be installed in the installation space 76*b* due to the separation-preventing section 77 formed to protrude from the insertion hole 76*a* when the band body 10 or the supporting band 30 is inserted to be installed in the insertion hole 76*a* of the fixing clip 75*a*.

Meanwhile, in one embodiment of the present invention, the insertion hole 76*a* of the fixing clip 75*a* for enabling the band body 10 or the supporting band 30 to be inserted is formed in an approximate staple shape alternately arranged at both top and bottom of the center thereof. However, as shown in FIG. 8, the fixing clip 75*b* may be formed an approximate U shape including the insertion hole 76*a* formed at the top for enabling the band body 10 or the supporting band 30 to be inserted and the installation space 76*b* in which the band body 10 or the supporting band 30 inserted through the insertion hole 76*a* is installed but is not limited thereto.

Here, at least one separation-preventing section 77 is formed to protrude at each of both sides of the end portion of the insertion hole 76*a* of the fixing clip 75*b* and the separation-preventing sections 77 formed to protrude from both sides of the insertion hole 76*a* are formed in the wedge shape including the incline 77*a* formed at one side to enable the band body 10 or the supporting band 30 to be easily inserted and the preventing surface 77*b* formed at the other side for preventing the inserted band body 10 or supporting band 30 from being separated and released outward.

Also, in the embodiment, two separation-preventing sections 77 are formed to protrude from the both sides of the insertion hole 76*a* of the fixing clip 75*b*. However, the number of the separation-preventing sections 77 is not limited thereto and may be variously changed.

Meanwhile, in one embodiment of the present invention, the fixing clips 75*a* and 75*b* are formed in the staple shape or the U shape including the insertion hole 76*a* for enabling the band body 10 or the supporting band 30 to be inserted to be installed. However, as long as the head cushion 70 is easily fixed to the band body 10 or the supporting band 30, the fixing clips 75*a* and 75*b* may be formed as a snap fastener or Velcro.

The bent member 79 is for connecting the fixing clips 75*a* and 75*b* with the main body 71, connects both ends of the fixing clips 75*a* and 75*b* with each edge of the main body 71, and moves due to a pressure.

Here, the bent member 79 is formed of an elastic material which moves upward, downward, leftward, and rightward and is bent to be modified in shape due to the pressure and is restored to an original shape when the pressure is released.

For this, the bent member 79 may be formed to be thinner than thicknesses of the fixing clips 75*a* and 75*b* and the main body 71 to be easily modified in shape by the pressure and restored but is not limited thereto.

Meanwhile, a bent hole 79*a* in a slot shape is formed to pass through the bent member 79 and the bent member 79 more easily becomes modified and restored due to the bent hole 79*a*.

In one embodiment of the present invention, the bent hole 79*a* formed to pass through each of the bent members 79 is formed in the slot shape. However, the bent hole 79*a* may be formed in a circular shape, an elliptical shape, or in various other shapes and is not limited thereto.

Also, in one embodiment of the present invention, one bent hole 79*a* is formed to pass through each of the bent members 79. The number of the bent holes 79*a* formed to pass through each of the bent members 79 is not limited thereto and a length, a width, and the like of the bent hole 79*a* may be variously changed.

Due to a structure as described above, when the head cushion 70 is installed at the headband 1 and used, the bent member 79 of the head cushion 70 is bent by a pressure of the welding mask 3 and the like and due to this gaps between the fixing clips 75*a* and 75*b* and the main body 71 become narrower and buffer the weight and load of the welding mask 3.

Hereinafter, a process of installing the functional/multi-purpose head cushion for a headband will be described with reference to FIGS. 10 to 13.

First, the head cushion 70 is installed in the headband 1 applied to industrial safety equipment such as the welding mask 3, the safety face shield, a hard hat, a helmet or the like and medical supplies such as a medical head guard, a safety hat, a medical helmet and the like.

Here, the head cushion 70 is installed at the headband 1 by inserting and installing the insertion hole 76*a* of the head cushion 70 at which the fixing clip 75*a* in approximately ⊏-shape is formed into the band body 10 or the supporting band 30 of the headband 1.

When the band body 10 or the supporting band 30 is inserted and installed in the installation space 76*b* through a side of the insertion hole 76*a* of the fixing clip 75*a* of the head cushion 70 formed in the staple shape, the band body 10 or the supporting band 30 is guided by the inclines 77*a* of the separation-preventing sections 77 formed to protrude from the top and bottom of the insertion hole 76*a* and inserted and installed in the installation space 76*b*.

Since the separation-preventing sections 77 are formed to protrude from the top and bottom of the insertion hole 76*a*, when the band body 10 or the supporting band 30 is inserted and installed in the fixing clip 75*a*, the insertion hole 76*a* is partially extended as the band body 10 or the supporting band 30 is guided by the inclines 77*a* of the separation-preventing sections 77 formed at the insertion hole 76*a* and the insertion hole 76*a* is restored to be an original shape as the band body 10 or the supporting band 30 passes the inclines 77*a* of the separation-preventing sections 77 and are coupled to the installation space 76*b*.

The band body 10 or the supporting band 30 inserted and installed in the installation space 76*b* of the fixing clip 75*a* as described above touches the preventing surfaces 77*b* of the separation-preventing sections 77 formed to protrude from the top and bottom of the insertion hoe 76*a* and is prevented from being separated and released outside the fixing clip 75*a*.

Meanwhile, when the head cushion 70 is separated from the band body 10 or the supporting band 30, the insertion hole 76*a* of the fixing clip 75*a* is partially extended and then the band body 10 or the supporting band 30 coupled to the installation space 76*b* is separated to release.

Here, when the fixing clip 75*b* of the head cushion 70 is formed in a U shape, the band body 10 or the supporting band 30 is inserted and installed in the installation space 76*b* through the insertion hole 76*a* formed above of the fixing clip 75*b* while being guided along the inclines 77*a* of the separation-preventing sections 77 formed to protrude from the both sides of the insertion hole 76*a*, and prevented by the preventing surfaces 77*b* of the separation-preventing sections 77 formed to protrude form the both sides of the insertion hole 76*a* from being separated and released.

As shown in FIGS. 12 and 13, the head cushion 70 as described above is installed at the headband 1 provided in various types of industrial safety equipment such as the welding mask 3, a safety face shield, a hard hat, a helmet and the like and medical supplies such as a medical head guard, a safety hat, a medical helmet and the like and then the length of the adjustable band 20 connected to the band body 10 is adjusted by adjusting the length adjusting lever 50 of the headband 1 after the headband 1 at which the head cushion 70 is installed is worn to be adequate for the size or perimeter of the head of the wearer.

Here, since the vulnerable portion in the center of the head of the wearer is not pressurized while worn due to the openings 71*a* and 71*b* formed at the head cushion 70, comfortable fit may be provided and simultaneously a pressure and pain caused by pressurizing may be prevented.

Also, ventilation and airing at the head of the wearer may be easily performed by the openings 71*a* and 71*b* formed at the main body 71 of the head cushion 70 while the headband 1 is worn and due to this perspiration while the wearer works for a long time may be minimized.

As described above, a supported range at the head is extended by installing the head cushion 70 at the headband 1 and a contact area between the head cushion 70 and the head is reduced by forming the openings at the main body 71 of the head cushion 70 to pass therethrough, thereby distributing the weight and load of the welding mask 3 and the like to release pressure on the wearer.

Also, since flexibility is added and elastic efficiency is improved by the incised portion 72*a* formed at the head cushion 70, the head cushion 70 may flexibly come into close contact with the head of the wearer while the head cushion 70 is worn, may be flexibly bent according to the weight and load of the welding mask 3 and the like to more easily distribute the load to easily release the pressure on the wearer, and may be flexibly bent upward, downward, leftward, and rightward to come into close contact with the size and shape of the head of the wearer to increase working efficiency and effectiveness.

Meanwhile, since flexibility of the main body 71 is more improved to easily distribute the weight and load and simultaneously is flexibly bent upward, downward, leftward, rightward, and in various directions by improving elastic efficiency of the main body 71 by the bent portions 72*b* formed in a semicircular shape at the main body 71 of the head cushion 70, wearability and comfortablity may be provided and a state of being in comfortably close contact with the head may be maintained regardless of a movement such as operations after worn.

Also, due the bent sections 72*c* formed to be bent by a certain angle at the edge of the main body 71 of the head cushion 70, the head cushion 70 may be stably worn and mounted on the head while worn and simultaneously an accident such as a scratch at the head caused by the edge end may be prevented.

Here, the soft portion 73 formed of a soft material is formed at the bottom surface of the main body 71 of the head cushion 70 and touches the head of the wearer when the head cushion 70 is worn, thereby minimizing the pressure on the head of the wearer and simultaneously preventing the head cushion 70 from falling off from the head.

Meanwhile, the auxiliary pad 74 formed of paper or fabric may be provided at the bottom of the main body 71 of the head cushion 70 to prevent pressurizing such as a weight, a load, and the like on the head of the wearer.

Also, the bent members in the stepped shape formed to be bent several times extends from the edge end of the main body 71 of the head cushion 70 and the bent member in the stepped shape first coming into contact with the head of the wearer is folded and comes into close contact therewith and the like to be sequentially/gradually worn on the head of the wearer, thereby distributing and simultaneously buffering the weight and load.

Here, when a load is added by a weight of industrial safety equipment while the headband 1 applied to industrial safety equipment such as the welding mask 3, a safety face shield, a hard hat, a helmet and the like and medical supplies such as a medical head guard, a safety hat, a medical helmet and the like, the bent members 79 which connect the fixing clips 75*a* and 75*b* with the main body 71 of the head cushion 70 are bent and modified in shape and gaps between the fixing clips 75*a* and 75*b* and the main body 71 become narrower, thereby buffering the load of the welding mask 3 and the like.

Here, modifications in shape caused by applying pressure and restoration are easily performed by the bent holes 79*a* formed to pass through the bent members 79.

Meanwhile, as shown in FIG. 12, since a supported area is extended by inserting and installing the head cushion 70 in the second supporting band 33 among the supporting band 30 of the headband 1, positioned at the top of the head of the wearer to support the head, the head cushion 70 may be worn regardless of the shape and size of the head.

Also, as shown in FIG. 13, since a supported area is extended by inserting and installing the head cushion 70 in the first supporting band 31 positioned at a top of the frontal region of the wearer to support the head and the second supporting band 33 among the supporting band 30 of the headband 1, the head cushion 70 may be worn regardless of the shape and size of the head.

In one embodiment of the present invention, the head cushion 70 is worn after inserted and installed in the first supporting band 31 of the supporting band 30 or after inserted and installed in each of the first supporting band 31 and the second supporting band 33 of the supporting band 30. However, the head cushion 70 may be worn on the second supporting band 33 of the supporting band 30.

Also, in one embodiment of the present invention, the head cushion 70 is configured to be installed at the first supporting band 31 or the second supporting band 33 of the supporting band 30 or the first and second supporting bands 31 and 33 to support and buffer the head of the wearer. However, the head cushion 70 may be configured to be installed at the band body 10 to support and buffer the head of the wearer.

Also, in one embodiment of the present invention, the head cushion 70 is configured to be inserted and installed in a central portion of the first supporting band 31 or the second supporting band 33 of the supporting band 30 to be worn. However, to be adequate for the shape or size of the head of the wearer, at least one head cushion 70 may be inserted in and installed at both sides of the central portion of the first supporting band 31 or both sides of the central portion of the second supporting band 31 or the head cushion 70 may be inserted in and installed at to be biased toward one side or the other side of the first supporting band 31 or the second supporting band 33 and then worn.

Although particular embodiments of the present invention have been described, one of ordinary skill in the art should easily understand that various modifications and changes can be made without departing from the concept of the present invention defined by the scope of the following claims.

| (Description of Reference Numerals) | | | |
|---|---|---|---|
| 1: | Headband | 3: | Welding Mask |
| 10: | Band Body | 20: | Adjustable Band |
| 30: | Supporting Band | 31: | First Supporting Band |
| 33: | Second Supporting Band | 50: | Length Adjusting Lever |
| 50a: | Lever | 70: | Head Cushion |
| 71: | Main Body | 71a, 71b: | Openings |
| 72a: | Incised Portion | 72b: | Bent Portion |
| 72c: | Bent Section | 73: | Soft Portion |
| 74: | Auxiliary Pad | 75a, 75b: | Fixing Clips |
| 76a: | Insertion Hole | 76b: | Installation Space |
| 77: | Separation-Preventing Section | 77a: | Incline |
| 77b: | Preventing Surface | 79: | Bent Member |
| 79a: | Bent Hole | | |

The invention claimed is:

1. A functional/multi-purpose head cushion for a headband comprising a band body configured to be worn on a head of a wearer, a supporting band connected to the band body and supported by a top of the head of the wearer, an adjustable band connected to a rear end of the band body and configured to be adjusted in length, and a length adjusting lever configured to adjust the length of the adjustable band, the head cushion comprising:
   a main body formed to be concave from top, bottom, left, and right toward the center thereof;
   a fixing clip provided at an upper portion of the main body and configured to receive one of the band body and the supporting band, the fixing clip defining an insertion hole that is configured to enable the one of the band body and the supporting band to be inserted and installed therein;
   a bent member connecting both end portions of the fixing clip with an upper portion of an edge of the main body to be integrated therewith; and
   separating-preventing sections protruding inwardly toward each other from opposing sides of the fixing clip,
   wherein the head cushion is formed with an elastic material to be easily modified and restored in shape, inserted, and installed in the headband to complementarily support the head of the wearer,
   wherein the fixing clip and the bent member are in an opening of the main body and are movable in the opening relative to the main body.

2. The headed cushion of claim 1, wherein at least one opening extends through the main body.

3. The head cushion of claim 1, wherein at least one incised portion is formed at the main body.

4. The head cushion of claim 1, wherein at least one bent portion is formed at the main body to be bent in a semicircular shape.

5. The head cushion of claim 1, wherein a bent section bent by a certain angle is formed at an edge end portion of the main body.

6. The head cushion of claim 1, wherein a soft portion comprising a soft material is formed at a bottom surface of the main body.

7. The head cushion of claim 1, wherein an auxiliary pad mounted at a lower portion of the main body and comprising a paper or fabric material is provided.

8. The head cushion of claim 1, wherein the fixing clip is U-shaped.

9. The head cushion of claim 1, wherein the bent member includes at least one bent hole, and wherein the at least one bent hole has a slot-shaped and extends through the bent member.

10. The head cushion of claim 1, wherein the fixing clip and the bent member are movable vertically and elastically in the opening relative to the main body.

11. A functional/multi-purpose head cushion for a headband comprising a band body configured to be worn on a head of a wearer, a supporting band connected to the band body and supported by a top of the head of the wearer, an adjustable band connected to a rear end of the band body and configured to be adjusted in length, and a length adjusting lever configured to adjust the length of the adjustable band, the head cushion comprising:
   a main body formed to be concave from top, bottom, left, and right toward the center thereof;
   a fixing clip provided at an upper portion of the main body and configured to receive one of the band body and the supporting band, the fixing clip having an insertion hole at one side thereof that defines a bottom and is configured to enable the one of the band body and the supporting band to be inserted and installed therein;
   a bent member connecting both end portions of the fixing clip with an upper portion of an edge of the main body to be integrated therewith; and
   a separating-preventing section including a wedge that protrudes from the bottom of the insertion hole,
   wherein the head cushion is formed with an elastic material to be easily modified and restored in shape, inserted, and installed in the headband to complementarily support the head of the wearer,
   wherein the fixing clip and the bent member are in an opening of the main body and are movable in the opening relative to the main body.

12. The head cushion of claim 11, wherein the fixing clip is C-shaped.

13. The head cushion of claim 11, wherein the bent member includes at least one bent hole, and wherein the at least one bent hole has a slot-shaped and extends through the bent member.

14. The head cushion of claim 11, wherein the separation-preventing section also includes a preventing surface that cooperates with the wedge to prevent the band body or the supporting band inserted therein from being separated therefrom.

15. The head cushion of claim 11, wherein the fixing clip and the bent member are movable vertically and elastically in the opening relative to the main body.

* * * * *